United States Patent [19]

Purdue et al.

[11] Patent Number: 5,356,808
[45] Date of Patent: Oct. 18, 1994

[54] HIGHLY FERMENTABLE, HIGH MALTOSE, NON-CRYSTALLIZING STARCH CONVERSION SYRUP

[75] Inventors: James C. Purdue, West Lafayette, Ind.; Kevin D. Kapper, Decatur, Ill.; Michael D. Bunch, Forsyth, Ill.; Jerry L. Turner, Shelbyville, Ill.

[73] Assignee: A.E. Staley Manufacturing Company, Decatur, Ill.

[21] Appl. No.: 178,226

[22] Filed: Jan. 6, 1994

Related U.S. Application Data

[63] Continuation-in-part of Ser. No. 41,952, Apr. 2, 1993, abandoned.

[51] Int. Cl.$^5$ .............. C12P 19/00; C12P 19/22; C12P 19/20; C12P 19/14
[52] U.S. Cl. .............. 435/254.2; 435/72; 435/95; 435/96; 435/99; 435/240.31
[58] Field of Search .............. 435/95, 96, 98, 99, 435/72, 240.31, 254.2; 536/123.1, 123.13

[56] References Cited

U.S. PATENT DOCUMENTS

| | | | |
|---|---|---|---|
| 2,891,869 | 6/1959 | Langlois | 426/48 |
| 3,067,066 | 12/1962 | Ehrenthal et al. | 127/38 |
| 3,137,639 | 6/1964 | Hurst et al. | 435/96 |
| 3,329,578 | 7/1967 | Faucett et al. | 435/96 |
| 3,565,765 | 2/1971 | Hendy et al. | 435/95 |
| 3,630,844 | 12/1971 | Hurst et al. | 435/95 |
| 3,644,126 | 2/1972 | Bodnar et al. | 426/48 |
| 3,677,896 | 7/1972 | Kurimoto et al. | 435/95 |
| 3,783,100 | 1/1974 | Larson et al. | 435/95 |
| 3,791,865 | 2/1974 | Hurst et al. | 127/32 |
| 3,963,575 | 6/1976 | Bulich | 435/98 |
| 4,028,186 | 6/1977 | Sakai | 435/99 |
| 4,032,403 | 6/1977 | Sakai et al. | 435/95 |
| 4,052,226 | 10/1977 | Verbanac | 127/29 |
| 4,199,372 | 4/1980 | Walon | 127/40 |
| 4,410,368 | 10/1983 | Takasaki et al. | 127/38 |
| 4,445,938 | 5/1984 | Verwaerde et al. | 127/29 |
| 4,647,538 | 3/1987 | Zeikus et al. | 435/201 |
| 5,112,407 | 5/1992 | Sakai et al. | 127/58 |

OTHER PUBLICATIONS

Houng et al., "Production of High Maltose Syrup Using an Ultra-filtration Reactor," Bioprocess Engineering 8:85-90 (1992).

Abstract No. 92-171634/21, "High Maltotriose Concn. Compsn. for Sweetening-Prepd. by Sepg. Chromatographically Maltotriose Soln. Contg. Maltose and Other Sugars Using Cation Exchange Resin".

*Primary Examiner*—Douglas W. Robinson
*Assistant Examiner*—Michael V. Meller
*Attorney, Agent, or Firm*—Arnold, White & Durkee

[57] ABSTRACT

A highly fermentable, high maltose, non-crystallizing starch conversion syrup is produced having a minimum fermentable equivalent of 95%, a maltose content ranging from about 40 to 65%, a dextrose content ranging from about 35 to 50%, a maltotriose content of less than about 3%, and a dextrose content plus maltose content of at least 93%. The methods for producing the above-described syrup comprise either a one-stage conversion of an α-amylase thinned syrup using a mixture of enzymes, comprising a barley β-amylase, a pullulanase, and a blend of a glucoamylase and a pullulanase or a two-stage conversion of an α-amylase thinned syrup, comprising two enzymatic conversions, the first using a mixture of α-amylase, maltogenic α-amylase, and pullulanase enzymes, and the second using glucoamylase and pullulanase enzymes.

3 Claims, No Drawings

HIGHLY FERMENTABLE, HIGH MALTOSE, NON-CRYSTALLIZING STARCH CONVERSION SYRUP

This is a continuation-in-part application of U.S. Ser. No. 08/041,952, filed Apr. 2, 1993, now abandoned.

BACKGROUND OF THE INVENTION

1. Field of the Invention

This invention relates broadly to highly fermentable, high maltose, non-crystallizing starch conversion syrups and to methods of producing such syrups. More specifically, the invention concerns an enzymatic method of making and the composition of a starch conversion syrup having high F.E. (fermentable equivalent) values, while reducing or eliminating the need for separation techniques involving crystallization, chromatography, membranes and the like. The syrups of the invention are especially characterized by their high content of maltose and low content of maltotriose (DP3) and higher saccharides.

2. Description of the Prior Art

The basic technology of producing syrups from starch, often referred to as starch conversion syrups, is well known. Commercially, the most important starch conversion syrup is made from corn starch, and hence is called "corn syrup." A substantial demand exists for special corn syrups which are highly fermentable, i.e., have a high F.E. value, preferably greater than about 90 percent.

High F.E. corn syrups are in particular demand as a brewing adjunct by brewers, and especially those brewers making light beers. These syrups generally have higher dextrose content than maltose content. Both dextrose and maltose are totally fermentable; however, dextrose, unlike maltose, produces negative effects on yeast in the brewing process when the dextrose concentration is high which for the purposes of the present invention is greater than 50% (w/w). High concentrations of dextrose are reported to cause decreased viability of the yeast in the fermentation process and to produce objectionable flavors in the finished beer. Therefore, the dextrose content in the present composition is preferred to be 50% or less.

The purpose behind the use of corn syrups with particularly high F.E. values in the brewing of light beers is that virtually all of the sugars contained in the corn syrup are consumed in the fermentation process and leave very little carbohydrate residue behind in the finished beverage. Thus, the calorie content of the "light" beer is less than other beers containing the extra carbohydrate residue.

A number of high maltose syrups are currently available in the marketplace. These syrups generally have a maltose content of 35% or greater. Generally, these syrups have an F.E. of only about 80% or less. Unfortunately, these syrups contain large levels of higher saccharides with a DP (degree of polymerization) greater than DP3. These higher saccharides are resistant to fermentation and consequently these sugars will remain in the finished beer raising the calorie content. Thus, these syrups are unacceptable for producing light beer.

The use of β-amylase enzymes to convert liquified starch to a high maltose syrup is well known. Commercially available syrups made in this manner attain maltose contents of from 35 to 65%. These syrups, however, are generally unacceptable for brewing light beers as they have an F.E. of less than 90%, meaning that at least 10% of the sugars are not fermentable and will remain in the finished beer.

High maltose syrups of about 80% maltose are also presently known in the art. To produce such a high maltose syrup generally requires that either the higher saccharides in the syrup be removed by methods involving chromatographic or membrane separation, or that the maltose be isolated by crystallization. Obviously, these methods entail certain costs and inefficiencies.

SUMMARY OF THE INVENTION

The present invention is directed toward a highly fermentable, high maltose, non-crystallizing starch conversion syrup which is particularly useful in the brewing of light beers. More particularly, the syrup of the present invention has a minimum F.E. of 95%, allowing for almost total conversion of the sugars in the syrup to alcohol when used in a fermentation process. The actual makeup of the syrup is about 40 to 65% maltose, about 35 to 50% dextrose, and less than about 3% maltotriose (DP3). Additionally, when the dextrose content (D) and maltose content (M) of the syrup are added the total is preferably 93% or greater. The syrup also preferably contains a minimum solids loading of 70% d.s. (dry solids). This makeup maximizes the fermentable portion of the syrup and minimizes the marginally fermentable maltotriose content of the syrup. The balance of the syrup is comprised of higher polymerized saccharides which are resistant to fermentation and are kept to less than about 5% of the total sugars.

The method of the present invention in a broad aspect comprises the enzymatic conversion of an enzymatically thinned corn syrup to produce a high maltose content corn syrup as described above. The method may be carried out in one or two enzymatic conversion stages, and makes it possible to avoid using physical separation procedures such as chromatography, membrane separation and the like to achieve high maltose content and high F.E. values.

When the method of the present invention is performed in one stage, the feed is preferably an α-amylase thinned corn syrup. Typically, the feed corn syrup may have about 30% or more d.s. and pH of about 4.5. The feed syrup is diluted with water until the dissolved solids content is about 25% d.s. and the feed syrup is adjusted with $Na_2CO_3$ or NaOH to a pH ranging from about 5.5 to 5.7.

The thinned feed syrup is treated with a mixture of enzymes, specifically a barley β-amylase, a pullulanase and a glucoamylase/pullulanase blend. This mixture of enzymes converts the thinned feed syrup to the highly fermentable, high maltose syrup of the present invention.

During the conversion, the temperature is maintained between about 50° C. and 63° C., preferably about 57° C.; the pH is maintained between about 4.5 and 6.5, preferably about 5.5; and the reaction is allowed to proceed for a time sufficient to produce the syrup of the present invention, but preferably about 24 hours. Experimental data indicate that reaction times of about 24 hours are sufficient to perform this conversion.

When the method of the present invention is performed in two stages, the feed to the first stage of the process of the invention is preferably an α-amylase thinned corn syrup. Typically, the feed corn syrup may have about 30% or more d.s. and a pH ranging from about 4.5 to 4.8. The feed syrup to the first stage is diluted with water until the dissolved solids content of the syrup is about 25% d.s. and the feed syrup is adjusted with $Na_2CO_3$ or NaOH to a pH ranging from about 5.5 to 5.7.

In the first stage, the thinned syrup feed is treated with a mixture of enzymes, including an α-amylase, to effect a first, partial conversion of the starch present to sugars. Other enzymes present in the first stage preferably include a β-amylase and a pullulanase. The first stage is kept at a temperature between about 50° C. and 63° C., preferably about 57° C.; a pH between about 4.5 and 6.5, preferably about 5.4; and a reaction time sufficient to produce an F.E. ranging from 80 to 94%. Reaction times of between about 20 and 50 hours are contemplated to be sufficient as indicated by experimental data.

Following the first stage or at a time overlapping the latter portions of the first stage, the two-stage method of the invention enters a second conversion stage in which the partially converted syrup is treated with one or more enzymes including glucoamylase at the same general conditions of pH and temperature as in the first stage. A preferred enzyme mixture for use in this stage comprises glucoamylase and pullulanase, wherein the enzymes primarily act to convert the sugars present to dextrose.

The conversion in stage two is allowed to proceed for a time sufficient to produce a product having an F.E. value of at least about 95% and a DP3 value less than about 3%. Times for the conversion in this stage are contemplated to be between about 15 and 35 hours, as determined by experimentation.

While high maltose syrups containing about 80% maltose are known, as are methods that may produce them, a unique part of the present invention is the use of a β-amylase enzyme, either prior to or in combination with a glucoamylase enzyme. Glucoamylase enzymes are generally known to hydrolyze terminal glucose residues from higher saccharides; and glucoamylase is normally expected to predominantly produce dextrose. Because this action is known, one skilled in the art would be lead to believe that the enzymatic conversion using glucoamylase would break down higher saccharides to dextrose and also break down maltose to dextrose. In fact, some dextrose is apparently produced at the expense of maltose; however, the higher saccharides are affected to a greater extent than the maltose and the maltose content of the syrup remains unexpectedly large.

After an appropriate conversion time for either the one-stage or two-stage method, the enzymatic conversion is terminated by inactivating the enzymes. Thereafter, the syrup is refined by conventional techniques.

Specifically, the converted syrup is filtered using microfiltration and the filtrate (permeate) is saved. The filtered syrup is then fed through a column of decolorizing resin. Following the decolorizing step, the filtered syrup is collected in a tank and the pH adjusted to a range of about 3.5 to 4.8. The syrup is then passed through a bed of strong acid cation exchange resin in the $H^+$ form followed by a bed of weak base anion exchange resin in the free base form. The pH is then adjusted to about 4.5 to 4.8 with dilute HCl. Finally, the syrup is evaporated giving a final syrup of at least 70% d.s. and loaded in drums for storage.

DETAILED DESCRIPTION OF THE INVENTION

Throughout the disclosure and claims of this application, certain abbreviations will be used. These abbreviations have the following meanings.

"F.E." is an abbreviation for "fermentable equivalent." The F.E. is determined from a liquid chromatography saccharide profile and is defined by the following equation: % F.E. = % Dextrose + % Maltose + 80% of the % Maltotriose (only about 80% of the DP3 sugars are fermentable). Thus, the percent F.E. is an expression of the fermentable sugars present in a given syrup.

The enzyme amylo-1,6-glucosidase often referred to as pullulanase is capable of selectively hydrolyzing α-1,6-glucosidic bonds of the amylopectin fraction of starch. Other enzymes capable of hydrolyzing α-1,6-glucosidic bonds are referred to in the literature as isoamylases. This type of enzyme generally acts to debranch the branched starch molecules.

β-amylase enzymes are generally exo-acting enzymes producing β-maltose by catalyzing the hydrolysis of maltose units from non-reducing ends of starch. That is, these enzymes selectively remove maltose units working from the non-reducing ends of the starch.

Glucoamylase enzymes generally hydrolyze terminal glucose residues from non-reducing ends of starch and glycogen forming β-dextrose. Comparing the action of a β-amylase with a glucoamylase, a β-amylase selectively removes two joined dextrose residues, i.e., one maltose residue and a glucoamylase selectively removes single dextrose residues.

Alpha amylase enzymes bypass α-1,6-glucosidic linked branch points in branched starches, releasing α-1,4-glucosidic bonds. Alpha amylase enzymes randomly break α-1,4-glucosidic bonds and produce minimal amounts of glucose and maltose.

The process of the present invention used in making highly fermentable, high maltose, non-crystallizing starch conversion syrup is less expensive and requires less equipment than other commercial processes. Generally, to achieve a maltose syrup of the same fermentable equivalent, the enzymatically converted syrup must be treated after conversion to remove the DP3 and larger sugars. Such techniques as chromatographic separation, membrane separation, or crystallization are generally used. Obviously, these additional processes increase the cost and decrease the efficiency of producing the highly fermentable, high maltose syrup. The process of the present invention accomplishes the same result by enzymatic conversion alone.

The highly fermentable, high maltose, non-crystallizing starch conversion syrup of the present invention has a minimum fermentable equivalent or F.E. of 95%. The syrup contains from about 40 to 65% maltose, about 35 to 50% dextrose, and less than about 3% DP3 sugars, such that the D plus M is greater than or equal to 93. The balance of the syrup is made up of DP4+ sugars. Preferably, the syrup will contain a minimum dry solids loading of 70% d.s. This syrup benefits from having an extremely low DP3 content, as those sugars having a degree of polymerization of 3 or more are increasingly resistant to fermentation.

The process for producing the highly fermentable, high maltose, non-crystallizing starch conversion syrup begins with obtaining a starch conversion syrup having a D.E. in the range of about 6 to 20%. An especially preferred starting syrup would be one having a D.E. of about 10. For the present invention, this syrup is preferably produced by the process disclosed in U.S. Pat. No. 3,783,100. The process disclosed in the '100 patent is incorporated herein by reference.

Based on actual tests of the invention, a specific embodiment of the process may be carried out as described below. Using a batch enzyme conversion process, a 10 D.E. α-amylase thinned syrup of about 32% d.s. and a pH ranging from about 4.5 to 4.8 is obtained. The temperature of the syrup is maintained in a temperature range from about 57° C. to 60° C. The 10 D.E. thinned syrup is diluted to about 25% d.s. with water and the pH increased to a range from about 5.5 to 5.7 using a solution of soda ash. The entire mixture is deposited in a tank. The tank is filled to above the agitator. Thereafter, the following enzymes are added: Promozyme 460, a pullulanase (having an activity of 460 PUN/gm) made by Novo Nordisk, in a concentration of 0.1732% (w/w dsb); Maltogenase 4000L, maltogenic α-amylase made by Novo Nordisk (having an activity of 4000 MANU/ml), in a concentration of 0.4315% (w/w dsb); and BAN 240L, an α-amylase (having an activity of 240 KNU/gm) made by Novo Nordisk, in a concentration of 0.0994% (w/w dsb). The enzymatic conversion is allowed to proceed until the F.E. has reached between about 80 and 94%. The time required for a proper first conversion may range from 20 to 50 hours. Experimentation has shown about 41 hours to be an especially preferred time. The temperature remains at about 57° C., as that is the temperature at which the enzymes used are most effective; however, the temperature may range from about 50° to 63° C. After about 41 hours of enzyme conversion, Dextrozyme 225/75, a glucoamylase-pullulanase enzyme blend (having an activity of 225 AGU/ml and 75 PUN/ml, respectively) made by Novo Nordisk, is added in a concentration of 0.0226% (w/w dsb). The second enzyme conversion step is allowed to proceed until the F.E. has reached at least 95%. The time required for a proper second conversion may range from about 15 to 35 hours. Experimentation has shown that a particularly preferred time is between 26 and 27 hours. During the second conversion, the temperature remains constant at about 57° C.; however may range from about 50° to 63° C. The pH is held at about 5.4; however it may range from about 4.5 to 6.5.

It is contemplated that the glucoamylase enzyme added for the second enzymatic conversion of the syrup may be added at an earlier point with the same results. That is, rather than waiting for the first enzymatic conversion to reach an F.E. of 80 to 94%, the glucoamylase enzyme may be added earlier and achieve the same composition of the syrup of the present invention.

The first conversion is allowed to proceed for a period of time ranging from about 30 to 50 hours; however, as noted earlier, an especially preferred time has been demonstrated through experimentation to be about 41 hours. The first conversion primarily produces maltose. As the first conversion progresses, the F.E. begins to plateau, generally between 80 and 94%, indicating the need for a second conversion.

The second conversion primarily produces dextrose and therefore must be observed relatively closely so as not to over convert the sugars present, in particular, the maltose. Once the F.E. has reached 95% or more, generally taking from 15 to 35 hours, the second conversion may be terminated.

Experimentation has shown that the syrup of the present invention can be produced in one stage. A 10 D.E. α-amylase thinned syrup is prepared for conversion as described above. The entire mixture is deposited in a tank. The tank is filled to above the agitator. Thereafter, the following enzymes are added: Spezyme BBA 1500, a barley β-amylase (having an activity of 1500 D.P.° per milliliters) made by Genencor International, in a concentration of 0.12% (w/w dsb); Promozyme 460, a pullulanase (having an activity of 460 PUN/gm) made by Novo Nordisk, in a concentration of 0.638% (w/w dsb); and Dextrozyme 225/75, a glucoamylase/pullulanase enzyme blend (having an activity of 225 AGU/ml and 75 PUN/ml, respectively) made by Novo Nordisk, is added in a concentration of 0.0452% (w/w dsb). The enzymatic conversion is allowed to proceed until the F.E. has reached 95% or greater and the dextrose and maltose contents of converted syrup reach the proper ranges. The time required for this conversion is about 24 hours.

One skilled in the art understands that enzyme concentrations are time dependent. Thus, generally, if the enzyme concentration is doubled, the conversion time will be about one-half of that disclosed. Conversely, generally, if the enzyme concentration is halved, the conversion time will be about double that disclosed.

Regardless of whether the enzymatic conversion is done in one or two stages, when the conversion has proceeded to the proper end point, the conversion is terminated by lowering the pH to about 4 and increasing the temperature of the converted syrup to about 80° C. The temperature is held at that temperature for approximately two hours to deactivate the enzymes. The syrup is then pumped from the tank for refining.

The converted syrup is cooled to about 60° C. and filtered using a four-inch spiral wound microfiltration membrane. Only the filtrate (permeate) is saved. Insoluble inclusions in the syrup, like lipids, proteins, and unhydrolyzed starch are removed by the microfiltration step. This same result could be achieved by filtration of the syrup using conventional diatomaceous earth.

The filtered syrup is maintained at about 60° C. and fed through a column of decolorizing resin (Dow XUS 40390), a column of Dow 88 strong acid cation resin (H+ form), and a column of Dow 66 weak base anion resin (free base form). All the resins are properly conditioned and regenerated prior to passing the filtered syrup through them. The filtration steps primarily remove objectionable flavors, odors and colors from the converted syrup. As a result of the filtration steps, the DP4+ fraction present in the syrup may be slightly reduced but the reduction is inconsequential for the purposes of the present invention.

The refined syrup is then collected in a tank and maintained at about 60° C. and the pH is maintained in a range from about 3.5 to 4.8. When all of the syrup from the refining run has been collected, a final pH adjustment is made to give a pH ranging from about 4.5 to 4.8. Either dilute HCl or dilute soda ash is used as necessary. The syrup is then evaporated on a single effect, plate and frame APV evaporator to give a final dry solids content of at least 70% d.s. The finished syrup is then loaded into a 55-gallon drum.

The refined syrup of the present invention obtains certain benefits from a solids loading of at least 70% d.s. and preferably 75% d.s. Specifically, the syrup enjoys a much greater shelf stability. Generally, refined corn syrups with low solids loadings act as a very good medium for bacteria and yeast growth during storage; however, by greatly reducing the water content and thereby increasing the solids content, the potential for bacteria and yeast growth is greatly reduced. Thus, the storage stability of the refined syrup is increased tremendously. An additional benefit to the manufacturer is reduced shipping costs. This is because the manufacturer does not have to pay to ship the water present in refined syrups having lower solids content and higher water content.

As solids loadings increase in refined corn syrups, there may be a tendency for crystallization to occur. Crystallization has adverse effects on shipping and storage of refined corn syrups. In particular, crystallization during shipping, especially if shipping is by tank car or tank truck, may render the syrup virtually unusable.

The syrup of the present invention, when refined, is clear and free of crystals. This is the result of favorable concentrations of dextrose and maltose in spite of high solids loadings.

The following examples are provided so as to enable those of ordinary skill in the art to make the compositions of the invention. These examples are not intended to limit the scope of what the inventors regard as their invention. Efforts have been made to ensure accuracy with respect to numbers used to characterize the measured conditions; however, some experimental errors and deviations may be present.

EXAMPLE 1

A 10 D.E. enzyme thinned, 25% d.s. starting syrup was converted using 0.1808% Promozyme 460, 0.4315% Maltogenase 4000L, and 0.1028% BAN 240L. The conversion was allowed to proceed for approximately 41 hours at a temperature of about 57° C. and a pH of about 5.4. After 41 hours, 0.0225% Dextrozyme 225/75 was added and a second conversion allowed to proceed for between 26 and 27 hours. The conditions of the second conversion were, a temperature of about 57° C. and a pH of about 5.4. The resulting syrup had the desired F.E. and D.E., the desired maltose content, the desired dextrose content, the desired D+M value and the desired maltotriose content.

EXAMPLE 2

A 10 D.E. enzyme thinned, 25% d.s. starting syrup was converted using 0.1200% Spezyme BBA 1500L, and 0.638% Promozyme 200L (having an activity of 161 PUN/gm, determined by assay). Conversion was allowed to proceed for a period of about 24 hours at a temperature of about 57° C. and a pH of about 5.4. After 24 hours, 0.0452% Dextrozyme 225/75 was added and a second conversion allowed to occur. The second conversion was allowed to proceed for about 21 hours at a temperature of about 57° C. and a pH of about 5.4. The resulting syrup had the desired F.E., D.E., maltose content, dextrose content, D+M value and maltotriose content.

EXAMPLE 3

A 10 D.E. enzyme thinned, 25% d.s. starting syrup was converted using 0.1200% Spezyme BBA 1500L, 0.638% Promozyme 200L (having an activity of 161 PUN/gm, determined by assay), and 0.0452% Dextrozyme 225/75. Conversion was allowed to proceed for a period of about 24 hours at a temperature of about 57° C. and a pH ranging from about 5.5 to 5.7. The resulting syrup had the desired F.E., D.E., maltose content, dextrose content, D+M value and maltotriose content.

EXAMPLE 4

A 10 D.E. enzyme thinned, 25% d.s. starting syrup was converted using 0.2000% Spezyme BBA 1500L, 0.638% Promozyme 200L (having an activity of 161 PUN/gm, determined by assay), and 0.0452% Dextrozyme 225/75. Conversion was allowed to proceed for a period of about 24 hours at a temperature of about 57° C. and a pH ranging from about 5.5 to 5.7. The resulting syrup had the desired F.E., D.E., maltose content, dextrose content, D+M value and maltotriose content.

EXAMPLE 5

A 10 D.E. enzyme thinned, 25% d.s. starting syrup was converted using 0.2000% Spezyme BBA 1500L, 0.638% Promozyme 200L (having an activity of 161 PUN/gm, determined by assay), and 0.0350% Dextrozyme 225/75. Conversion was allowed to proceed for a period of about 24 hours at a temperature of about 57° C. and a pH ranging from about 5.5 to 5.7. The resulting syrup had the desired F.E., D.E., maltose content, dextrose content, D+M value and maltotriose content.

EXAMPLE 6

A 10 D.E. enzyme thinned, 25% d.s. starting syrup was converted using 0.1200% Spezyme BBA 1500L, 0.638% Promozyme 200L (having an activity of 161 PUN/gm, determined by assay), and 0.0350% Dextrozyme 225/75. Conversion was allowed to proceed for a period of about 24 hours at a temperature of about 57° C. and a pH ranging from about 5.5 to 5.7. The resulting syrup had the desired F.E., D.E., maltose content, dextrose content, D+M value and maltotriose content.

The results of the above examples are illustrated in Table 1 as follows:

TABLE 1

| EX. | F.E. | D+M | Dextrose | Maltose | DP3 | DP4 | DP5 | DP6 |
| --- | --- | --- | --- | --- | --- | --- | --- | --- |
| 1 | 96.00 | 93.90 | 36.49 | 57.41 | 2.62 | 2.50 | 0.23 | 0.17 |
| 2 | 96.56 | 95.10 | 48.99 | 46.11 | 1.82 | 0.96 | 0.15 | 0.17 |
| 3 | 95.95 | 94.39 | 44.58 | 49.81 | 1.85 | 1.80 | 1.54 | 0.33 |
| 4 | 95.85 | 94.20 | 43.67 | 50.53 | 2.01 | 1.83 | 1.55 | 0.36 |
| 5 | 95.26 | 93.35 | 35.35 | 58.00 | 2.33 | 2.19 | 1.49 | 0.59 |
| 6 | 95.25 | 93.32 | 35.69 | 57.63 | 2.36 | 2.18 | 1.42 | 0.68 |

Additional advantages and modifications will be readily apparent to those skilled in the art. The invention in its broader aspects is therefore not limited to the specific details or representative examples described. Accordingly, departures may be made from the detail without departing from the spirit or scope of the disclosed general inventive concept.

What is claimed is:

1. A highly fermentable, high maltose, non-crystallizing starch conversion syrup having a minimum fermentable equivalent of 95%, a maltose content ranging from about 40 to 65%, a dextrose content ranging from about 35 to 50%, a maltotriose content of less than 3% and a value for the dextrose content plus the maltose content of at least 93%.

2. The highly fermentable, high maltose, non-crystallizing syrup of claim 1 having a minimum dry solids content of 70%.

3. The highly fermentable, high maltose, non-crystallizing syrup of claim 1 having a minimum dry solids content of 75%.

* * * * *